(12) United States Patent
Yamaoka (10) Patent No.: US 8,210,349 B2
(45) Date of Patent: Jul. 3, 2012

(54) SENSOR STORAGE CONTAINER

(75) Inventor: Hideaki Yamaoka, Kyoto (JP)

(73) Assignee: ARKRAY, Inc., Kyoto (JP)

( * ) Notice: Subject to any disclaimer, the term of this patent is extended or adjusted under 35 U.S.C. 154(b) by 0 days.

(21) Appl. No.: 10/550,287

(22) PCT Filed: Mar. 25, 2004

(86) PCT No.: PCT/JP2004/004150
§ 371 (c)(1),
(2), (4) Date: Sep. 22, 2005

(87) PCT Pub. No.: WO2004/092720
PCT Pub. Date: Oct. 28, 2004

(65) Prior Publication Data
US 2006/0191813 A1    Aug. 31, 2006

(30) Foreign Application Priority Data
Mar. 25, 2003    (JP) .................................. 2003-083440

(51) Int. Cl.
*A61B 19/02* (2006.01)
*B65D 85/00* (2006.01)
*B65D 85/62* (2006.01)

(52) U.S. Cl. ....................... 206/438; 206/459.5; 206/499

(58) Field of Classification Search ................... 206/438, 206/499, 459.5, 718; 600/345; 204/403.01–403.15; 205/775, 777.5, 780.5, 792; 422/55–58
See application file for complete search history.

(56) References Cited

U.S. PATENT DOCUMENTS

| | | | | |
|---|---|---|---|---|
| 2,904,205 A | * | 9/1959 | Callery | 206/499 |
| 3,139,976 A | * | 7/1964 | Swain | 206/0.82 |
| 3,244,272 A | * | 4/1966 | Beaman et al. | 206/0.82 |
| 4,589,547 A | * | 5/1986 | Stewart et al. | 206/718 |
| 4,889,229 A | * | 12/1989 | Yamamoto et al. | 206/723 |
| 4,889,239 A | * | 12/1989 | Sandish et al. | 206/562 |

(Continued)

FOREIGN PATENT DOCUMENTS

AT    206585    12/1959

(Continued)

OTHER PUBLICATIONS

An Electrochemical Capillary Fill Device for the Analysis of Glucose Incorporating Glucose Oxidase and Ruthenium (III) Hexamine as Mediator, N. A. Morris, M. F. Cardosi, B. J. Birch, A. P. F. Turner, Electroanalysis, 1992, pp. 1-9.*

(Continued)

*Primary Examiner* — Bryon Gehman
(74) *Attorney, Agent, or Firm* — Morgan, Lewis & Bockius LLP (57) ABSTRACT

A sensor storage container is provided that allows sensors to be checked visually from the outside. A container is used for storing sensors including an oxidation-reduction enzyme that oxidizes or reduces an object to be analyzed, a mediator that mediates the transfer of electrons caused by oxidation or reduction, and a detection means that detects the oxidation or reduction reaction. The container is transparent or semi-transparent in whole or in part and thereby the sensors can be checked visually from the outside of the container. This container may be composed of a container body and a lid. The container body may be provided with a scale. Preferably, the sensors are those produced using a ruthenium metal complex as the mediator.

8 Claims, 3 Drawing Sheets

U.S. PATENT DOCUMENTS

| | | | |
|---|---|---|---|
| 5,084,041 A | | 1/1992 | Oxley et al. |
| 5,200,051 A | * | 4/1993 | Cozzette et al. ......... 204/403.07 |
| 5,205,920 A | | 4/1993 | Oyama et al. ................. 204/403 |
| 5,262,305 A | * | 11/1993 | Heller et al. ................ 205/780.5 |
| 5,447,229 A | * | 9/1995 | Lynch et al. .................. 206/499 |
| 5,657,198 A | * | 8/1997 | Flener ........................... 361/220 |
| 6,143,164 A | * | 11/2000 | Heller et al. ............... 205/777.5 |
| 6,146,510 A | | 11/2000 | Leader et al. |
| 6,175,752 B1 | * | 1/2001 | Say et al. ....................... 600/345 |
| 6,299,757 B1 | * | 10/2001 | Feldman et al. .............. 205/775 |
| 6,372,515 B1 | | 4/2002 | Casterlin et al. |
| 6,432,363 B2 | * | 8/2002 | Biebernik et al. ......... 422/82.07 |
| 6,461,496 B1 | * | 10/2002 | Feldman et al. ......... 204/403.03 |
| 6,464,849 B1 | * | 10/2002 | Say et al. ................. 204/403.01 |
| 6,603,318 B2 | * | 8/2003 | Hansen et al. ................ 206/438 |
| 6,605,200 B1 | * | 8/2003 | Mao et al. ................ 204/403.14 |
| 6,605,201 B1 | * | 8/2003 | Mao et al. ................ 204/403.14 |
| 6,676,816 B2 | * | 1/2004 | Mao et al. ................ 204/403.14 |
| 6,761,816 B1 | * | 7/2004 | Blackburn et al. ......... 205/777.5 |
| 7,501,053 B2 | * | 3/2009 | Karinka et al. ............... 205/792 |
| 2004/0079653 A1 | * | 4/2004 | Karinka et al. .......... 204/403.01 |

FOREIGN PATENT DOCUMENTS

| | | |
|---|---|---|
| AU | 790747 | 8/1997 |
| CN | 1340704 | 3/2002 |
| DE | 1 013 837 | 8/1957 |
| DE | 198 31 519 | 1/2000 |
| EP | 0 860 695 | 8/1998 |
| JP | 47-32548 | 9/1972 |
| JP | 56-123118 | 9/1981 |
| JP | 61-25179 | 2/1986 |
| JP | 62-067571 | 3/1987 |
| JP | H-0216484 | 2/1990 |
| JP | 2231558 | 9/1990 |
| JP | 6-222035 | 8/1994 |
| JP | 3018448 | 11/1995 |
| JP | 9-184837 | 7/1997 |
| JP | 9-222410 | 8/1997 |
| JP | 2000-210613 | 8/2000 |
| JP | 2000-314711 | 11/2000 |
| JP | 2001-141686 | 5/2001 |
| JP | 2001-225833 | 8/2001 |
| JP | 2002-122562 | 4/2002 |
| JP | 2003-42994 | 2/2003 |
| JP | 2003-072861 | 3/2003 |
| JP | 2003-215086 | 7/2003 |
| WO | 97/44672 | 11/1997 |
| WO | 00/29111 | 5/2000 |

OTHER PUBLICATIONS

Supplementary European Search Report issued in corresponding European Application No. 04723334.1 and mailed Mar. 13, 2009—3 pages.

Office Action dated Oct. 5, 2010 in corresponding Japanese Patent Application No. 2005-505350.

Office Action dated May 12, 2011 in corresponding Japanese Patent Application No. 2005-505350.

* cited by examiner

SENSOR STORAGE CONTAINER

TECHNICAL FIELD

The present invention relates to a sensor storage container that stores sensors to be used for analyzing an object to be analyzed through an oxidation-reduction reaction.

BACKGROUND ART

Conventionally, sensors are used widely for analyzing biogenic substances such as glucose, cholesterol, etc. For instance, a glucose sensor is used for the self-control of a diabetic's blood-sugar level. Generally, the glucose sensor is an electrode sensor in which a working electrode and a reference electrode are formed on a substrate, and reagents such as glucose oxidase and potassium ferricyanide are provided thereon. When this electrode sensor is placed in a measuring device and a diabetic puts his blood collected by himself onto the reagent part, the glucose oxidase oxidizes the glucose contained in the blood to cause electrons to be transferred and thereby the current value changes. The change in current value then is detected with the pair of electrodes and is measured with the measuring device to be converted into the blood-sugar level, which then is displayed. The potassium ferricyanide mediates the transfer of electrons caused through an oxidation-reduction reaction and thus is referred to as a mediator. This substance delivers electrons to and receives electrons from the electrodes. This transfer of electrons that occurs between the electrodes and the mediator is carried out at high speed, which results in a higher measuring speed. The sensor is stored in a container as one of a plurality of sensors and is taken out when it is used.

The container for the sensors, however, is not transparent and therefore the number of sensors cannot be checked visually from the outside. Accordingly, in order to check the number of sensors visually, it is necessary to open the container, which is inconvenient. In addition, the sensors are exposed to the outside air every time the number of sensors is checked visually, and this causes the sensors to deteriorate due to oxidization caused by or humidity brought by the air, which has been a problem.

DISCLOSURE OF INVENTION

The present invention was made in consideration of the aforementioned situations. An object of the present invention is to provide a sensor storage container that makes it possible to check the number of sensors visually from the outside without opening the container.

In order to achieve the above-mentioned object, the container of the present invention is a sensor container for storing sensors and is transparent or semi-transparent in part or in whole.

The sensor storage container of the present invention makes it possible to check the number of remaining sensors visually from the outside, and thus is not only convenient but also can prevent the sensors from deteriorating since the container is not opened every time the number of sensors is checked visually.

DESCRIPTION OF THE INVENTION

The type of sensors to be contained in the container of the present invention is not particularly limited and the sensors may have or may not have lightfastness. When lightfast sensors are to be stored, the transparent or semi-transparent part may be formed in any part of the container.

In the present invention, the word "transparent" or "semi-transparent" denotes a property that allows the sensors contained in the container to be checked visually from the outside.

When the sensors to be contained in the container of the present invention do not have lightfastness, it is preferable that only the bottom part of the container be transparent or semi-transparent. This makes it possible to see the sensors through the bottom part, only when the sensors are checked visually, and to prevent light from entering the container at any other times, which further can prevent the sensors from deteriorating.

Preferably, the container of the present invention has a scale for determining the number of the sensors. This is because the number of the sensors can be checked visually correctly when the scale is provided. When only the bottom part of the container is transparent or semi-transparent, it is more preferable that the container have the scale in its bottom part. The container of the present invention may be composed of a container body and a lid.

The material of the container according to the present invention is not particularly limited but a semi-transparent or transparent material is used for the semi-transparent or transparent part of the container. Examples of the semi-transparent material include bakelite, phenol resin, polyethylene, polysulfone, polycarbonate, ABS resin, polypropylene, vinyl chloride, epoxy resin, etc. Among them polyethylene, polypropylene, and vinyl chloride are preferable, and polyethylene and polypropylene are particularly preferable. Furthermore, the transparent material to be described below can be processed into a semi-transparent material through the addition of an additive such as a pigment. Examples of the transparent material include acrylic resin, polycarbonate, polysulfone, ABS resin, polyethylene, polypropylene, vinyl chloride, epoxy resin, etc. Among them polyethylene, polypropylene, and vinyl chloride are preferable, and polypropylene is particularly preferable.

Furthermore, an ultraviolet absorber may be added to the above-mentioned transparent material. Examples of the ultraviolet absorber include 2-(2'-hydroxy-5'-methylphenyl)benzotriazole, 2-(2'-hydroxy-3'-t-butyl-5'-methylphenyl)-5-chlorobenzotriazole, 2-(2'-hydroxy-3'5-di-t-butylphenyl)-5-chlorobenzotriazole, 2-hydroxy-4-n-octoxy-benzophenone, phenyl salicylate, etc.

In the present invention, the transparent or semi-transparent material denotes one that allows the sensors to be checked visually from the outside through the material.

In the container of the present invention, the transparent or semi-transparent part may be colored. In that case, examples of the color of the container include black, gray, brown, blue, green, red, yellow, and white. The color is preferably black, gray, brown, blue, or yellow and more preferably black, gray, or brown. Such coloring makes it possible to prevent sensors with poor lightfastness from deteriorating.

In the container of the present invention, the material of the part other than the transparent or semi-transparent part is not particularly limited. For instance, the above-mentioned transparent or semi-transparent materials can be used including bakelite, phenol resin, polyethylene, acrylic resin, polycarbonate, polysulfone, ABS resin, polypropylene, vinyl chloride, epoxy resin, etc.

The shape of the container of the present invention is not particularly limited. Examples of the shape include a rectangular parallelepiped shape, a cubic shape, a columnar shape, an elliptic cylinder shape, etc. The shape is determined suitably according to various conditions such as the shape, size, etc. of the sensors. The size of the container of the present invention also is not particularly limited but is determined suitably according to various conditions such as the shape, size, etc. of the sensors. For instance, when the container is of a rectangular parallelepiped shape, the size thereof is, for example, length 15 mm to 50 mm×width 15 mm to 50 mm×height 30 mm to 100 mm, preferably length 20 mm to 40 mm×width 20 mm to 40 mm×height 40 mm to 80 mm, and more preferably length 30 mm to 35 mm×width 30 mm to 35 mm×height 45 mm to 55 mm.

Figure 1:
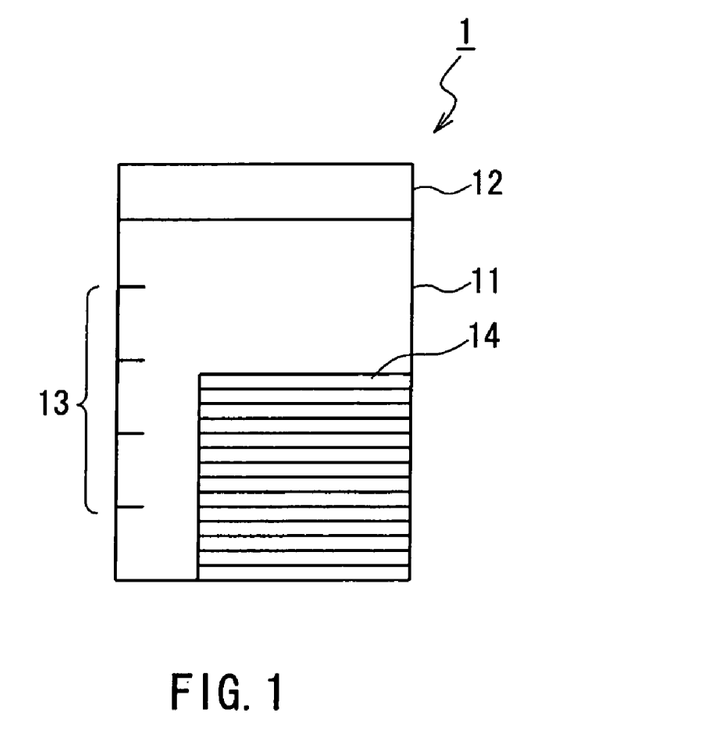
FIG. 1 is a diagram showing the configuration of an example of the container according to the present invention.
Figure 2:
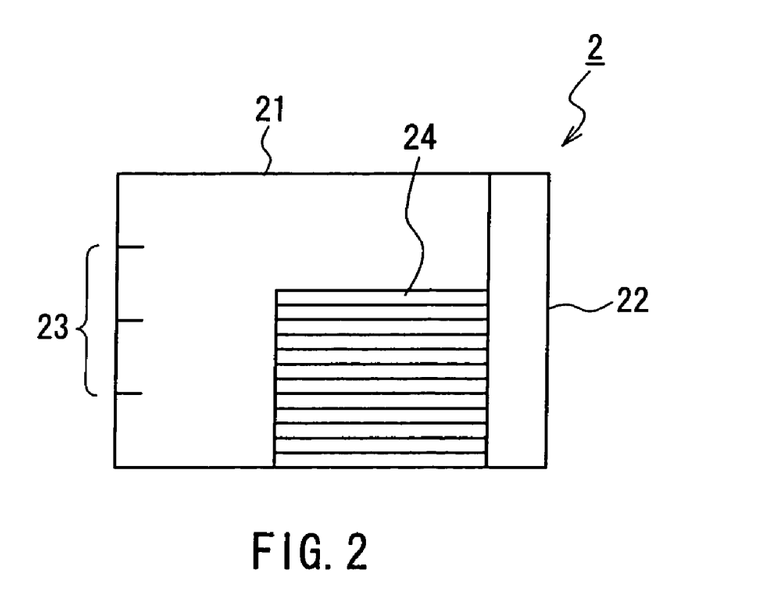
FIG. 2 is a diagram showing the configuration of another example of the container according to the present invention.

An example of the container of the present invention is shown in FIG. 1. As shown in FIG. 1, this sensor storage container 1 is composed of a container body 11 and a lid 12. The whole container body 11 is semi-transparent or transparent. The side face of the container body 11 is provided with a scale 13 in the height direction. In FIG. 1, numeral 14 indicates a plurality of sensors stored in the container. In addition, FIG. 2 shows an example in which the bottom part of the container is provided with a scale. As shown in FIG. 2, the sensor storage container 2 is composed of a container body 21 and a lid 22. The whole container body 21 is transparent or semi-transparent. Furthermore, the bottom part of the container body 21 has a scale. When the number of the sensors contained in this container is to be checked visually, the container simply is laid on its side. In FIG. 2, numeral 24 indicates a plurality of sensors stored in the container.

Figure 5A:
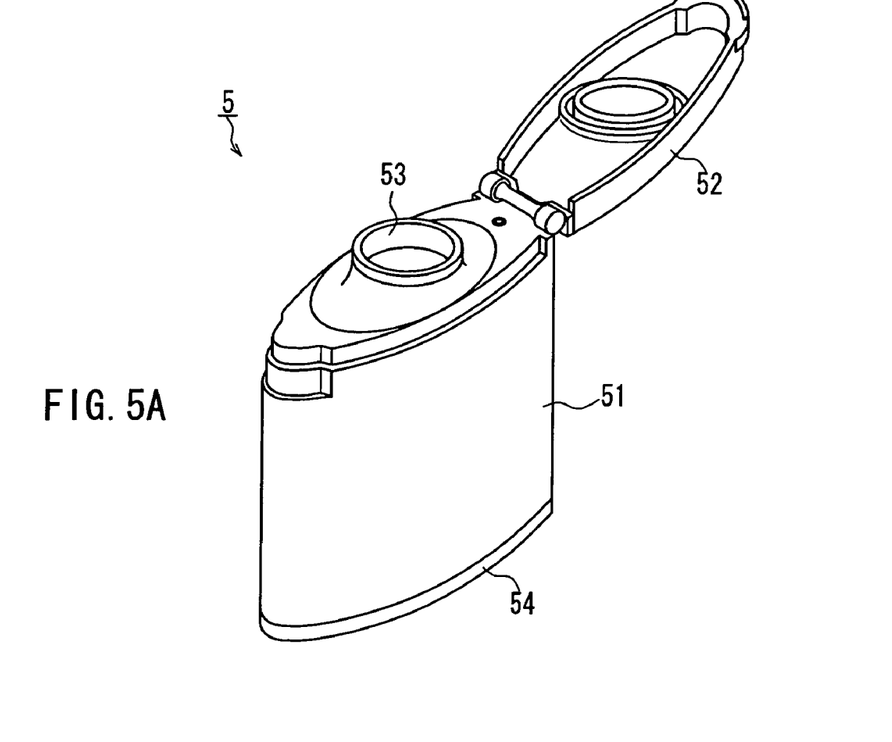
FIGS. 5A and 5B are a perspective view and a cross-sectional view showing another configuration of the container according to the present invention, respectively.
Figure 5B:
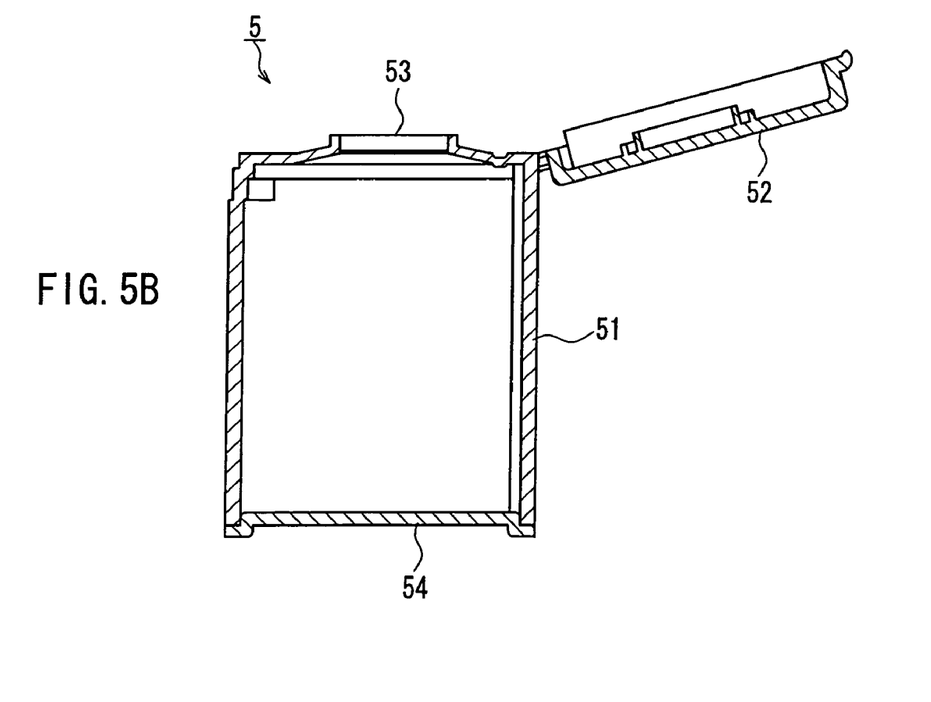

FIGS. 5A and 5B show a perspective view and a cross-sectional view of another example of the container according to the present invention. As shown in FIGS. 5A and 5B, the container 5 is composed of a container body 51 (transparent or semi-transparent), a top lid 52, and a bottom lid 54. The container body 51 has a circular opening 53 in the upper part thereof A circular projection of the top lid 52 can fit into the circular opening 53. Furthermore, the whole bottom part of the container body 51 is open and is closed with the bottom lid 54. This container 5 also may be provided with a scale for visually checking the number of the sensors. The size of the container with such a shape is not particularly limited but can be for instance, width 15 mm to 50 mm×length 15 mm to 50 mm×height 30 mm to 100 mm, preferably width 20 mm to 40 mm×length 20 mm to 40 mm×height 40 mm to 80 mm, and more preferably width 30 mm to 35 mm×length 30 mm to 35 mm×height 45 mm to 55 mm.

The method of manufacturing a container according to the present invention is not particularly limited but it can be manufactured by the following methods, for instance. Examples of the method of manufacturing a container that is transparent only in its bottom part include: a method including producing a body part colored with a pigment having a shielding property and a transparent or semi-transparent bottom part by injection molding as individual parts and then bonding them to each other; a method including two-color-molding a body part and a bottom part by injection molding and then further molding the molded product by biaxial stretching blow molding or the like; and a method including producing a container whose whole part is transparent or semi-transparent and then attaching a colored shrink film to the whole part except for the bottom part thereof. The bonding method is not particularly limited but can be carried out by ultrasonic welding, thermal welding, etc. or using an adhesive, a solvent, etc., for example. Among them the ultrasonic welding is preferable. Furthermore, the material of the shrink film is not particularly limited but can be, for instance, polyethylene, polypropylene, or vinyl chloride.

An example of the sensors to be stored in the container of the present invention is described next.

The sensors to be stored in the container of the present invention include, for instance, an oxidation-reduction enzyme, a mediator that mediates the transfer of electrons caused by oxidation or reduction, and a detection means that detects the oxidation-reduction reaction.

Preferably, the sensors have resistance to light (lightfastness). Examples of the specific means for providing the sensors with the resistance to light include using a lightfast transition metal complex as a mediator and using a shielding material as a composition material of the sensors. Examples of the lightfast transition metal complex include a copper complex, an iron complex, a ruthenium complex, and an osmium complex. Among them the ruthenium complex is preferable. The copper complex, iron complex, ruthenium complex, and osmium complex are described below in detail. The following complexes to be used herein can be commercially available products or may be prepared by conventionally well-known methods.

Copper Complex

A copper complex changes in color tone, for instance, from blue ($Cu^{2+}$) to reddish brown ($Cu^+$) through the transfer of electrons from an enzyme. Examples of the ligand of a copper complex include nitrogen containing ligands such as bipyridine, imidazole, amino acid, phenanthroline, ethylenediamine, etc. The bipyridine, imidazole, amino acid, ethylenediamine, and phenanthroline may be combined into mixed ligands.

When the ligand is bipyridine, the coordination number thereof is 4 or 6. From the viewpoint of stability, however, it is preferable that two bipyridines be coordinated. The bipyridines do not need to be substituted but a substituent may be introduced. The introduction of the substituent makes it possible to adjust, for instance, solubility, oxidation-reduction potential, etc. The sites of substitution include sites 4,4' and 5,5'. Examples of the substituents include: alkyl groups such as a methyl group, an ethyl group, a propyl group, etc.; amine groups such as a phenyl group, an amino group, etc.; alkoxyl groups such as a hydroxy group, a methoxy group, an ethoxy group, etc.; a carboxyl group; and halogen groups such as bromine, chlorine, iodine, etc.

Examples of the bipyridine copper complex include [Cu (bipyridine)$_2$], [Cu(4,4'-dimethyl-2,2'-bipyridine)$_2$], [Cu(4,4'-diphenyl-2,2'-bipyridine)$_2$], [Cu(4,4'-diamino-2,2'-bipyridine)$_2$], [Cu(4,4'-dihydroxy-2,2'-bipyridine)$_2$], [Cu(4,4'-dicarboxy-2,2'-bipyridine)$_2$], [Cu(4,4'-dibromo-2,2'-bipyridine)$_2$], [Cu(5,5'-dimethyl-2,2'-bipyridine)$_2$], [Cu(5,5'-diphenyl-2,2'-bipyridine)$_2$], [Cu(5,5'-diamino-2,2'-bipyridine)$_2$], [Cu(5,5'-dihydroxy-2,2'-bipyridine)$_2$], [Cu(5,5'-dicarboxy-2,2'-bipyridine)$_2$], [Cu(5,5'-dibromo-2,2'-bipyridine)$_2$], [Cu(bipyridine)$_3$], [Cu(4,4'-dimethyl-2,2'-bipyridine)$_3$], [Cu(4,4'-diphenyl-2,2'-bipyridine)$_3$], [Cu(4,4'-diamino-2,2'-bipyridine)$_3$], [Cu(4,4'-dihydroxy-2,2'-bipyridine)$_3$], [Cu(4,4'-dicarboxy-2,2'-bipyridine)$_3$], [Cu(4,4'-dibromo-2,2'-bipyridine)$_3$], [Cu(5,5'-dimethyl-2,2'- bipyridine)$_3$], [Cu(5,5'-diphenyl-2,2'-bipyridine)$_3$], [Cu(5,5'-diamino-2,2'-bipyridine)$_3$], [Cu(5,5'-dihydroxy-2,2'-bipyridine)$_3$], [Cu(5,5'-dicarboxy-2,2'-bipyridine)$_3$], [Cu(5,5'-dibromo-2,2'-bipyridine)$_3$], etc.

When the ligand is imidazole, the coordination number thereof is 4. Imidazole does not need to be substituted but a substituent may be introduced. The introduction of the substituent makes it possible to adjust, for instance, solubility, oxidation-reduction potential, etc. The sites of substitution include sites 2, 4, and 5. Examples of the substituents include: alkyl groups such as a methyl group, an ethyl group, a propyl group, etc.; amine groups such as a phenyl group, an amino group, etc.; alkoxyl groups such as a hydroxy group, a methoxy group, an ethoxy group, etc.; a carboxyl group; and halogen groups such as bromine, chlorine, iodine, etc.

Examples of the imidazole copper complex include [Cu(imidazole)$_4$], [Cu(4-methyl-imidazole)$_4$], [Cu(4-phenyl-imidazole)$_4$], [Cu(4-amino-imidazole)$_4$], [Cu(4-hydroxy-imidazole)$_4$], [Cu(4-carboxy-imidazole)$_4$], [Cu(4-bromo-imidazole)$_4$], etc.

The amino acid is arginine (L-Arg), for instance. An arginine copper complex has the advantage of high solubility. Furthermore, examples of the mixed ligands include a combination of bipyridine and imidazole and a combination of bipyridine and amino acid, specifically [Cu(imidazole)$_2$(bipyridine)] and [Cu(L-Arg)$_2$(bipyridine)]. The use of a mixed ligand allows the copper complex to be provided with various characteristics. For instance, the use of arginine improves the solubility of the complex.

Iron Complex

An iron complex changes in color tone, for instance, from a yellowish color ($Fe^{3+}$) to a reddish color ($Fe^{2+}$) through the transfer of electrons from an enzyme. Examples of the ligand of an iron complex include nitrogen containing ligands such as bipyridine, imidazole, amino acid, phenanthroline, ethylenediamine, etc. The bipyridine, imidazole, amino acid, phenanthroline, and ethylenediamine may be combined into mixed ligands.

When the ligand is bipyridine, the coordination number thereof is 6. The bipyridine does not need to be substituted but a substituent may be introduced. The introduction of the substituent makes it possible to adjust, for instance, solubility, oxidation-reduction potential, etc. The sites of substitution include sites 4,4' and 5,5'. Examples of the substituent include: alkyl groups such as a methyl group, an ethyl group, a propyl group, etc.; amine groups such as a phenyl group, an amino group, etc.; alkoxyl groups such as a hydroxy group, a methoxy group, an ethoxy group, etc.; a carboxyl group; and halogen groups such as bromine, chlorine, iodine, etc.

Examples of the bipyridine iron complex include [Fe(bipyridine)$_3$], [Fe(4,4'-dimethyl-2,2'-bipyridine)$_3$], [Fe(4,4'-diphenyl-2,2'-bipyridine)$_3$], [Fe(4,4'-diamino-2,2'-bipyridine)$_3$], [Fe(4,4'-dihydroxy-2,2'-bipyridine)$_3$], [Fe(4,4'-dicarboxy-2,2'-bipyridine)$_3$], [Fe(4,4'-dibromo-2,2'-bipyridine)$_3$], [Fe(5,5'-dimethyl-2,2'-bipyridine)$_3$], [Fe(5,5'-diphenyl-2,2'-bipyridine)$_3$], [Fe(5,5'-diamino-2,2'-bipyridine)$_3$], [Fe(5,5'-dihydroxy-2,2'-bipyridine)$_3$], [Fe(5,5'-dicarboxy-2,2'-bipyridine)$_3$], [Fe(5,5'-dibromo-2,2'-bipyridine)$_3$], etc.

When the ligand is imidazole, the coordination number thereof is 6. Imidazole does not need to be substituted but a substituent may be introduced. The introduction of the substituent makes it possible to adjust, for instance, solubility, oxidation-reduction potential, etc. The sites of substitution include sites 2, 4, and 5. Examples of the substituent include: alkyl groups such as a methyl group, an ethyl group, a propyl group, etc.; amine groups such as a phenyl group, an amino group, etc.; alkoxyl groups such as a hydroxy group, a methoxy group, an ethoxy group, etc.; a carboxyl group; and halogen groups such as bromine, chlorine, iodine, etc.

Examples of the imidazole iron complex include [Fe(imidazole)$_6$], [Fe(4-methyl-imidazole)$_6$], [Fe(4-phenyl-imidazole)$_6$], [Fe(4-amino-imidazole)$_6$], [Fe(4-hydroxy-imidazole)$_6$], [Fe(4-carboxy-imidazole)$_6$], [Fe(4-bromo-imidazole)$_6$], etc.

The amino acid is arginine (L-Arg), for instance. An arginine iron complex generally has the advantage of high solubility. Furthermore, examples of the mixed ligands include a combination of bipyridine and imidazole and a combination of bipyridine and amino acid, specifically [Fe(imidazole)$_2$(bipyridine)$_2$] and [Fe(L-Arg)$_2$(bipyridine)$_2$]. The use of a mixed ligand allows the complex to be provided with various characteristics. For instance, the use of arginine improves the solubility of the complex.

Ruthenium Complex

Examples of the ligand of a ruthenium complex include nitrogen containing ligands such as bipyridine, imidazole, amino acid, phenanthroline, ethylenediamine, etc. The bipyridine, imidazole, amino acid, phenanthroline, and ethylenediamine may be combined into mixed ligands.

When the ligand is bipyridine, the coordination number thereof is 6. The bipyridine does not need to be substituted but a substituent may be introduced. The introduction of the substituent makes it possible to adjust, for instance, solubility, oxidation-reduction potential, etc. The sites of substitution include sites 4,4' and 5,5'. Examples of the substituent include: alkyl groups such as a methyl group, an ethyl group, a propyl group, etc.; amine groups such as a phenyl group, an amino group, etc.; alkoxyl groups such as a hydroxy group, a methoxy group, an ethoxy group, etc.; a carboxyl group; and halogen groups such as bromine, chlorine, iodine, etc.

Examples of the bipyridine ruthenium complex include [Ru(bipyridine)$_3$], [Ru(4,4'-dimethyl-2,2'-bipyridine)$_3$], [Ru(4,4'-diphenyl-2,2'-bipyridine)$_3$], [Ru(4,4'-diamino-2,2'-bipyridine)$_3$], [Ru(4,4'-dihydroxy-2,2'-bipyridine)$_3$], [Ru(4,4'-dicarboxy-2,2'-bipyridine)$_3$], [Ru(4,4'-dibromo-2,2'-bipyridine)$_3$], [Ru(5,5'-dimethyl-2,2'-bipyridine)$_3$], [Ru(5,5'-diphenyl-2,2'-bipyridine)$_3$], [Ru(5,5'-diamino-2,2'-bipyridine)$_3$], [Ru(5,5'-dihydroxy-2,2'-bipyridine)$_3$], [Ru(5,5'-dicarboxy-2,2'-bipyridine)$_3$], [Ru(5,5'-dibromo-2,2'-bipyridine)$_3$], etc.

When the ligand is imidazole, the coordination number thereof is 6. Imidazole does not need to be substituted but a substituent may be introduced. The introduction of the substituent makes it possible to adjust, for instance, solubility, oxidation-reduction potential, etc. The sites of substitution include sites 2, 4, and 5. Examples of the substituent include: alkyl groups such as a methyl group, an ethyl group, a propyl group, etc.; amine groups such as a phenyl group, an amino group, etc.; alkoxyl groups such as a hydroxy group, a methoxy group, an ethoxy group, etc.; a carboxyl group; and halogen groups such as bromine, chlorine, iodine, etc.

Examples of the imidazole ruthenium complex include [Ru(imidazole)$_6$], [Ru(4-methyl-imidazole)$_6$], [Ru(4-phenyl-imidazole)$_6$], [Ru(4-amino-imidazole)$_6$], [Ru(4-hydroxy-imidazole)$_6$], [Ru(4-carboxy-imidazole)$_6$], [Ru(4-bromo-imidazole)$_6$], etc.

The amino acid is arginine (L-Arg), for instance. An arginine ruthenium complex has the advantage of high solubility. Furthermore, examples of the mixed ligands include a combination of bipyridine and imidazole and a combination of bipyridine and amino acid, specifically [Ru(imidazole)$_2$(bipyridine)$_2$] and [Ru(L-Arg)$_2$(bipyridine)$_2$]. The use of a mixed ligand allows the complex to be provided with various characteristics. For instance, the use of arginine improves the solubility of the complex.

The oxidation-reduction enzyme to be used for the sensors is not particularly limited but is determined suitably according to the measurement objective. Examples of the oxidation-reduction enzyme include glucose oxidase, glucose dehydrogenase, lactate dehydrogenase, cholesterol oxidase, etc.

The means of detecting the oxidation-reduction reaction of the sensors is not particularly limited. For example, in the case of an electrode sensor, the means of detecting the oxidation-reduction reaction is electrodes that detect the current produced by the oxidation or reduction of the mediator. On the other hand, in the case of a colorimetric sensor, the means of detecting the oxidation-reduction reaction is a pigment that is colored by the oxidation or reduction.

The configuration of the sensors is not particularly limited but a common configuration may be employed.

Figure 3:
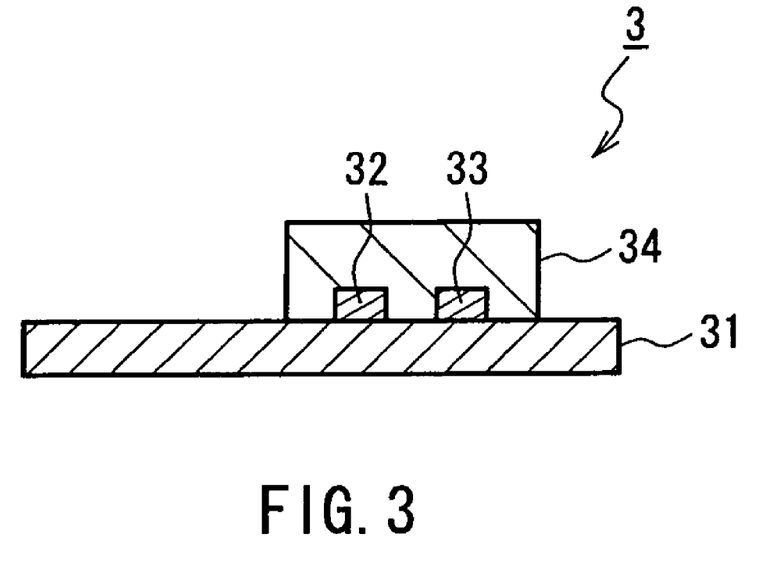
FIG. 3 is a cross-sectional view showing an example of the configuration of an electrode sensor.

FIG. 3 shows an example of the basic configuration of the electrode sensor. As shown in FIG. 3, in this electrode sensor 3, a pair of electrodes (a working pole 32 and a reference pole 33) is formed on a substrate 31, and a reagent layer including an oxidation-reduction enzyme and a mediator is formed thereon. This electrode sensor is stored in the container of the present invention and is taken out to be placed in a measuring device when it is used. Then a measuring object sample is allowed to adhere to the reagent layer 34 and thereby the oxidation-reduction enzyme causes an oxidation-reduction reaction. This is detected with the electrodes 32 and 33 as a change in current value and is converted into a predetermined constituent concentration by the measuring device, which then is displayed.

Figure 4:
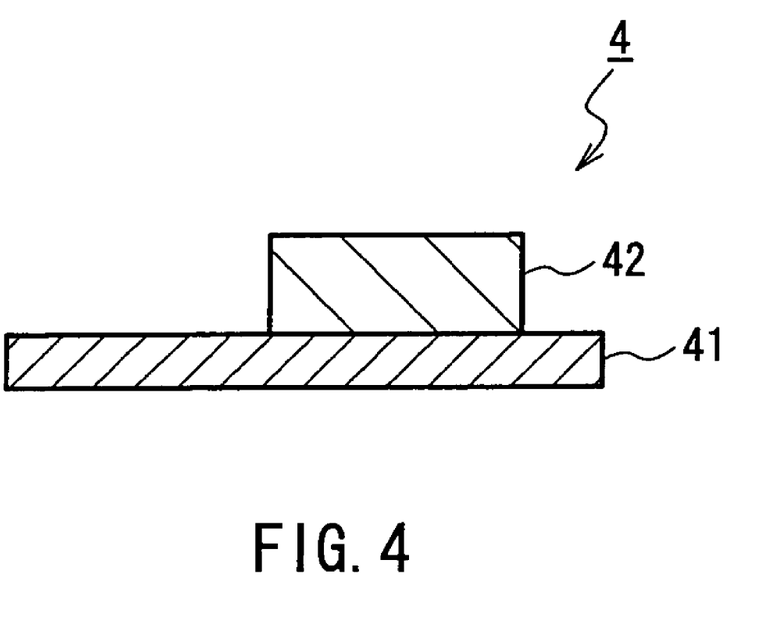
FIG. 4 is a cross-sectional view showing an example of the configuration of a colorimetric sensor.

FIG. 4 shows an example of the basic configuration of the colorimetric sensor. As shown in FIG. 4, in this colorimetric sensor 4, a reagent layer 42 including an oxidation-reduction enzyme, a color former (the substrate of the enzyme), and a mediator is formed on a substrate 41. This colorimetric sensor is taken out of the container of the present invention when it is used. Then a measuring object sample is allowed to adhere to the reagent layer 42 and thereby the oxidation-reduction enzyme causes an oxidation-reduction reaction, which results in coloring of the color former. The degree of this coloring is measured with an optical measuring apparatus such as a spectrophotometer and then is converted into a predetermined constituent concentration.

In the sensors described above, the reagent layers 34 and 42 may contain other components, for instance, hydrophilic polymers, a buffer, a stabilizer, etc.

EXAMPLES

Examples of the present invention are described next.

Example 1

Transparent Container

A container shown in FIGS. 5A and 5B that was transparent in whole was produced by injection molding using polypropylene as a material. The whole container has a size of width 20 mm×length 40 mm×height 55 mm. The upper circular opening has an inner diameter of 16 mm.

Container that is Transparent Only in its Bottom Part

A container shown in FIGS. 5A and 5B that was transparent only in its bottom part was produced by forming a body part having a shielding property and the transparent bottom part separately by injection molding using polypropylene as a material and then bonding them to each other by ultrasonic welding. The whole container has a size of width 20 mm×length 40 mm×height 55 mm. The upper circular opening has an inner diameter of 16 mm.

A glucose electrode sensor including a ruthenium complex used as a mediator or a glucose electrode sensor including potassium ferricyanide used as a mediator was placed in the transparent container and the container that was transparent only in its bottom part, which then were allowed to stand in a room for four days. Thereafter, the concentrations of the glucose solutions were measured. Furthermore, both the above-mentioned sensors were placed in shielding bottles that were used as controls, and the concentrations of the glucose solutions were measured in the same manner as above. These results are indicated in Tables 2 to 5 below. The container that was transparent only in its bottom part was allowed to stand still the bottom part down. Both the electrode sensors were produced by the following method. The concentrations of the glucose solutions were measured under the following conditions.

Production of Glucose Electrode Sensor

A glucose electrode sensor was produced that included a first electrode, a second electrode, a reagent layer, and a capillary that were formed on a substrate. The first electrode and the second electrode were formed by screen-printing them on the substrate with carbon ink and then drying them. The capacity of the capillary was set at 0.3 μL. The reagent layer had a two-layer structure composed of an electron transfer layer (a mediator layer) and an enzyme containing layer. The electron transfer layer was formed by applying 0.4 μL of a first material solution including an electron transfer material (the mediator: a ruthenium complex or potassium ferricyanide) to the substrate and then drying it through air blasting (at 30° C. and a relative humidity of 10%). The enzyme containing layer was formed by applying 0.3 μL of a second material solution including an oxidation-reduction enzyme to the electron transfer layer and then drying it through air blasting (at 30° C. and a relative humidity of 10%).

The first material solution was prepared as follows. That is, a liquid mixture obtained by mixing the materials (1) to (4), which are indicated in Table 1 below, together in the order of the numbers was allowed to stand for one to three days and then an electron transfer material was added thereto. The second material solution was prepared by dissolving an oxidation-reduction enzyme in 0.1% CHAPS.

TABLE 1

| Composition of First Material Solution (Except for Electron Transfer Material) | | | | | | |
|---|---|---|---|---|---|---|
| (1)SWN Solution | | (2)CHAPS Solution | | (3)Distilled Water | (4)ACES Solution | |
| Concentration | Amount | Concentration | Amount | | Concentration | Amount |
| 1.2% | 250 μL | 10% | 25 μL | 225 μL | 200 mM | 500 μL |

In Table 1, "SWN" denotes Lucentite, "CHAPS" indicates 3-[(3-choamidopropyl)dimethylammonio]-1-propanesulfonate, and "ACES" denotes N-(2-acetamido)-2-aminoethanesulfonic acid. The SWN used herein was a product No. 3150 manufactured by CO-OP CHEMICAL CO., LTD. The CHAPS and ACES used herein were products Nos. KC062 and ED067 manufactured by DOJINDO LABORATORIES.

The ACES solution was prepared so as to have a pH of 7.5.

The ruthenium (Ru) complex used herein was $[Ru(NH_3)_6]Cl_3$ (LM722, manufactured by DOJINDO LABORATORIES). The potassium ferricyanide ($K_3[Fe(III)(CN)_6]$) used herein was a product No. 28637-75 manufactured by Nacalai Tesque, Inc. The oxidation-reduction enzyme used herein was CyGDH. The CyGDH is composed of an alpha subunit, a beta subunit, and a gamma subunit.

Measurement of Glucose Solution Concentration

The electrode sensor was placed in a measuring device (a tester). Two types of glucose solutions whose concentrations were 0 mg/dL (deciliter) and 600 mg/dL were subjected to the measurement. The measured values were current values (μA) obtained 10 seconds after the application of constant potential (200 mV) to the electrodes.

TABLE 2

Glucose Concentration: 0 mg/dL
Sensors produced using Ru Complex

| Samples | Transparent Container (μA) | Container that was transparent only in its bottom part (μA) | Shielding Bottle (μA) |
|---|---|---|---|
| 1 | 0.17 | 0.16 | 0.21 |
| 2 | 0.19 | 0.18 | 0.14 |
| AVG | 0.18 | 0.17 | 0.17 |
| SD | 0.01 | 0.01 | 0.03 |
| CV(%) | 5.94 | 8.32 | 19.67 |

TABLE 3

Glucose Concentration: 600 mg/dL
Sensors produced using Ru Complex

| Samples | Transparent Container (μA) | Container that was transparent only in its bottom part (μA) | Shielding Bottle (μA) |
|---|---|---|---|
| 1 | 9.83 | 9.43 | 9.76 |
| 2 | 9.24 | 9.60 | 9.97 |
| 3 | 9.35 | 9.40 | 9.22 |
| 4 |  | 9.53 | 9.59 |
| AVG | 9.48 | 9.49 | 9.64 |
| SD | 0.26 | 0.09 | 0.27 |
| CV(%) | 2.71 | 0.97 | 2.84 |

TABLE 4

Glucose Concentration: 0 mg/dL
Sensors produced using potassium ferricyanide

| Samples | Transparent Container (μA) | Container that was transparent only in its bottom part (μA) | Shielding Bottle (μA) |
|---|---|---|---|
| 1 | 8.68 | 2.16 | 1.76 |
| 2 | 9.72 | 2.05 | 1.99 |
| 3 | 8.89 | 2.30 | 1.59 |
| AVG | 9.10 | 2.17 | 1.78 |
| SD | 0.45 | 0.13 | 0.16 |
| CV(%) | 4.93 | 5.77 | 9.15 |

TABLE 5

Glucose Concentration: 600 mg/dL
Sensors produced using potassium ferricyanide

| Samples | Transparent Container (μA) | Container that was transparent only in its bottom part (μA) | Shielding Bottle (μA) |
|---|---|---|---|
| 1 | 18.38 | 11.01 | 11.67 |
| 2 | 14.27 | 11.95 | 11.98 |
| 3 | 20.19 | 11.25 | 11.06 |
| AVG | 17.61 | 11.40 | 11.57 |
| SD | 2.48 | 0.40 | 0.38 |
| CV(%) | 14.08 | 3.50 | 3.30 |

As shown in Tables 2 to 5, when the electrode sensors produced using potassium ferricyanide were placed in the transparent container and then were allowed to stand in a room for four days, the potassium ferricyanide turned into potassium ferrocyanide due to light and thereby a considerable increase in background current (current obtained when the glucose concentration was 0 mg/dL) was observed. This means that an error as high as +50% is caused when being indicated in terms of the glucose concentration. When the electrode sensors were placed in the container that was transparent only in its bottom part and then were allowed to stand, no increase in background current was observed. Thus the measurement was carried out correctly, with no errors being caused, and less variations in measured value resulted. On the other hand, in the case of the electrode sensors produced using a ruthenium complex, even when they were placed in the transparent container and then were allowed to stand, no increase in background current was observed. Thus the measurement was carried out correctly, with no errors being caused, and less variations in measured value resulted.

Example 2

Two types of containers were produced as follows. Using them, the concentrations of glucose solutions were measured in the same manner as in Example 1. The results are indicated in Tables 6 to 9 below.

Semi-Transparent Only in Bottom Part

A container shown in FIGS. 6A and 5B that was semi-transparent only in its bottom part was produced using polypropylene as a material in the same manner as that employed for producing the container that was transparent only in its bottom part. In producing the bottom part, color pellets that were toned to deeper black were prepared first using a pigment (carbon black) (the ratio of the pigment contained in the pellets: 20 wt. %). The color pellets thus prepared and achromatic color pellets were mixed together at a mixing ratio of 5:100 so as to reach a critical point up to which the number of sensors can be checked visually. This was used to produce the bottom part. The whole container has a size of width 20 mm×length 40 mm×height 55 mm. The upper circular opening has an inner diameter of 16 mm.

Transparent Only in Bottom Part (Including an Ultraviolet Absorber Added Thereto)

A container shown in FIGS. 5A and 5B that was transparent only in its bottom part (including an ultraviolet absorber added thereto) was produced using polypropylene as a material in the same manner as that employed for producing the container that was transparent only in its bottom part. The material used for the bottom was that obtained by adding 2(2'-hydroxy-5'-methylphenyl)benzotriazole (3 wt. %) to the above-mentioned material. The whole container has a size of width 20 mm×length 40 mm×height 55 mm. The upper circular opening has an inner diameter of 16 mm.

TABLE 6

Glucose Concentration: 0 mg/dL
Sensors produced using Ru Complex

| Samples | Semi-Transparent only in Bottom Part (μA) | Transparent only in Bottom Part (including Ultraviolet Absorber) (μA) |
|---|---|---|
| 1 | 0.19 | 0.17 |
| 2 | 0.18 | 0.18 |
| AVG | 0.19 | 0.18 |
| SD | 0.01 | 0.01 |
| CV(%) | 3.82 | 4.04 |

TABLE 7

Glucose Concentration: 600 mg/dL
Sensors produced using Ru Complex

| Samples | Semi-Transparent only in Bottom Part (μA) | Transparent only in Bottom Part (including Ultraviolet Absorber) (μA) |
|---|---|---|
| 1 | 9.71 | 9.24 |
| 2 | 9.28 | 9.85 |
| 3 | 9.46 | 9.46 |
| 4 | 9.6 | 9.53 |
| AVG | 9.51 | 9.52 |
| SD | 0.19 | 0.25 |
| CV(%) | 1.95 | 2.65 |

TABLE 8

Glucose Concentration: 0 mg/dL
Sensors produced using Potassium Ferricyanide

| Samples | Semi-Transparent only in Bottom Part (μA) | Transparent only in Bottom Part (including Ultraviolet Absorber) (μA) |
|---|---|---|
| 1 | 2.13 | 1.97 |
| 2 | 1.86 | 2.07 |
| 3 | 2.1 | 2.34 |
| AVG | 2.03 | 2.13 |
| SD | 0.15 | 0.19 |
| CV(%) | 7.29 | 9.00 |

TABLE 9

Glucose Concentration: 600 mg/dL
Sensors produced using Potassium Ferricyanide

| Samples | Semi-Transparent only in Bottom Part (μA) | Transparent only in Bottom Part (including Ultraviolet Absorber) (μA) |
|---|---|---|
| 1 | 12.32 | 11.86 |
| 2 | 11.98 | 12.11 |

TABLE 9-continued

Glucose Concentration: 600 mg/dL
Sensors produced using Potassium Ferricyanide

| Samples | Semi-Transparent only in Bottom Part (μA) | Transparent only in Bottom Part (including Ultraviolet Absorber) (μA) |
|---|---|---|
| 2 | 11.22 | 11.03 |
| AVG | 11.84 | 11.67 |
| SD | 0.46 | 0.40 |
| CV(%) | 3.88 | 3.90 |

As shown in Tables 6 to 9, no increases in background current of the sensors produced using potassium ferricyanide and the sensors produced using a ruthenium complex were observed in either of the containers. Thus the measurement was carried out correctly, with no errors being caused, and less variations in measured value resulted.

INDUSTRIAL APPLICABILITY

The container of the present invention allows the numbers of remaining sensors to be checked visually from the outside and thus is convenient.

The invention claimed is:

1. A sensor-container combination comprising a transparent or semi-transparent container comprising at least one of polypropylene and polyethylene, wherein the container comprises a container body, a lid and a bottom part; and
a plurality of unshielded sensors stored in the container, wherein
the sensors each include
an oxidation-reduction enzyme;
a ruthenium complex; and
a means for detecting changes in current resulting from action of the oxidation-reduction enzyme.

2. The sensor-container combination according to claim 1, wherein the container has a scale for determining the number of the sensors in the container.

3. The sensor-container combination according to claim 1, wherein the sensors have lightfastness.

4. The sensor-container combination according to claim 1, wherein the detection means is electrodes that detect current produced by oxidation or reduction of the ruthenium complex, and the sensors are electrode sensors.

5. The sensor-container combination according to claim 1, wherein the detection means is a substrate of the oxidation-reduction enzyme that colors through oxidation or reduction, and the sensors are colorimetric sensors.

6. The sensor-containing combination according to claim 1, wherein
the container body has a circular opening,
the lid has a circular projection, and
the circular projection of the lid is capable of fitting into the circular opening of the container body.

7. The sensor-container combination according to claim 1, wherein the container body and the lid are connected to each other with a hinge.

8. The sensor-container combination according to claim 1, wherein a color of the bottom part of the container is selected from the group consisting of black, gray, brown, blue, green, red, yellow, and white.

* * * * *